United States Patent [19]

Spike

[11] Patent Number: 5,750,075
[45] Date of Patent: May 12, 1998

[54] CHROMOTOGRAPHY VIAL

[75] Inventor: Frederick W. Spike, Wilmington, N.C.

[73] Assignee: Sun International Trading, Ltd., Wilmington, N.C.

[21] Appl. No.: 601,684

[22] Filed: Feb. 15, 1996

[51] Int. Cl.$^6$ ....................................................... B01L 3/00
[52] U.S. Cl. .................. 422/102; 422/104; 206/446; 220/23.83; 220/408
[58] Field of Search .................................. 422/102, 104, 422/99; 436/174; 220/410, 23.83, 400, 408, 699; 215/12.1, 395, 100 R; 206/446

[56] References Cited

U.S. PATENT DOCUMENTS

| | | | |
|---|---|---|---|
| 3,807,955 | 4/1974 | Note, Jr. et al. | 422/102 |
| 4,015,941 | 4/1977 | Kurata | 422/102 |
| 4,094,641 | 6/1978 | Friswell | 422/102 |
| 4,227,620 | 10/1980 | Conway | 215/355 |
| 4,517,851 | 5/1985 | Tice | 73/864.91 |
| 4,534,465 | 8/1985 | Rothermal et al. | 206/443 |
| 5,137,693 | 8/1992 | Mawhirt | 422/104 |
| 5,167,929 | 12/1992 | Korf et al. | 422/102 |
| 5,186,339 | 2/1993 | Heissler | 211/74 |
| 5,350,564 | 9/1994 | Mazza et al. | 422/63 |
| 5,382,409 | 1/1995 | Baxter et al. | 422/102 |
| 5,397,542 | 3/1995 | Nelms et al. | 422/104 |
| 5,470,537 | 11/1995 | Siegel | 422/104 |

*Primary Examiner*—Long V. Le
*Attorney, Agent, or Firm*—Rhodes, Coates & Bennett, L.L.P.

[57] ABSTRACT

A sampling vial includes a generally cylindrical vial body having first and second reduced diameter sections axially spaced from one another. The first and second reduced diameter sections are aligned along a vertical axis of the vial and preferably have the same inside diameter. The reduced diameter sections function to vertically align a matching vial insert along the longitudinal axis of the sampling vial.

11 Claims, 3 Drawing Sheets

CHROMOTOGRAPHY VIAL

FIELD OF THE INVENTION

The present invention relates generally to glass vials for laboratory use, and more particularly to glass chromatography vials particularly adapted for microsampling.

BACKGROUND OF THE INVENTION

Laboratory analysis of a large number of samples is commonly accomplished by using an autosampler. Vials containing the samples are placed in a sample tray on the autosampler. The sample tray is indexed to position each sample vial below a needle assembly in succession. Alternately, the needle assembly may be indexed while the sample tray remains stationary. Each time the sample tray or needle assembly is indexed, the needle assembly is lowered into the vial to extract the sample. After the sample is obtained from the vial, the needle assembly is raised and the sample tray or needle assembly is indexed to position the next vial below the needle assembly. This process is repeated until a sample has been obtained from each sample vial.

Each type of autosampler is designed to receive vials of certain standard dimensions. For example, many autosamplers are designed to work with vials having an outside diameter of approximately 12 mm and an overall length of approximately 32 mm. A standard 12 mm by 32 mm vial typically has a volume of approximately 1.5 ml. These vials work well in most applications where the sample volume is greater than 250 μl. However, for samples smaller than 250 μl, the autosampler may not be able to extract enough sample to perform the desired analysis. This is because the needle assembly does not reach the bottom of the sample vial. Thus, there is a dead volume between the bottom of the vial and the tip of the needle assembly.

To work with small sample volumes, it is necessary to use vials having a smaller inside diameter which results in greater vertical displacement of the sample. However, these smaller vials typically do not fit into the sample trays of the autosampler. To overcome this problem, it is common practice to place a smaller diameter vial, known as an insert, into a larger standard vial designed to fit in the sample tray of the autosampler. Thus, the larger vial acts as a carrier for the smaller vial which contains the sample.

One problem which has been frequently encountered when using an insert is that the insert is not held vertically in the carrier vial. The bottom surface of the larger vial typically has a slightly concave bottom surface. This concave bottom surface pushes the tip of the insert to one side causing the insert to assume a tilted position in the vial. Because the insert is tilted, the needle of the autosampler may contact the inner surface of the insert which frequently results in the bending or breaking of the needle, or the breaking of the vial.

SUMMARY OF THE INVENTION

The present invention is a sampling vial particularly designed for use with a tubular vial insert. The sampling vial of the present invention comprises a generally cylindrical vial body having a closed bottom end and an open top. First and second reduced diameter sections are formed in the vial body and are axially spaced from one another. The first and second reduced diameter sections are axially aligned along the vertical axis of the vial body and preferably have the same inside diameter. When a matching vial insert is inserted into the vial of the present invention, the reduced diameter sections of the vial serve as guides to vertically align the vial insert within the vial.

The sampling vial of the present invention prevents the vial insert from tilting in the vial as was common with prior art vials. Thus, the vial of the present invention reduces the risk of damage to either the needle assembly or the vial insert. The sampling vial of the present invention may also be used without a vial insert in the same manner as a conventional straight-bodied vial.

DETAILED DESCRIPTION OF THE INVENTION

Figure 1:
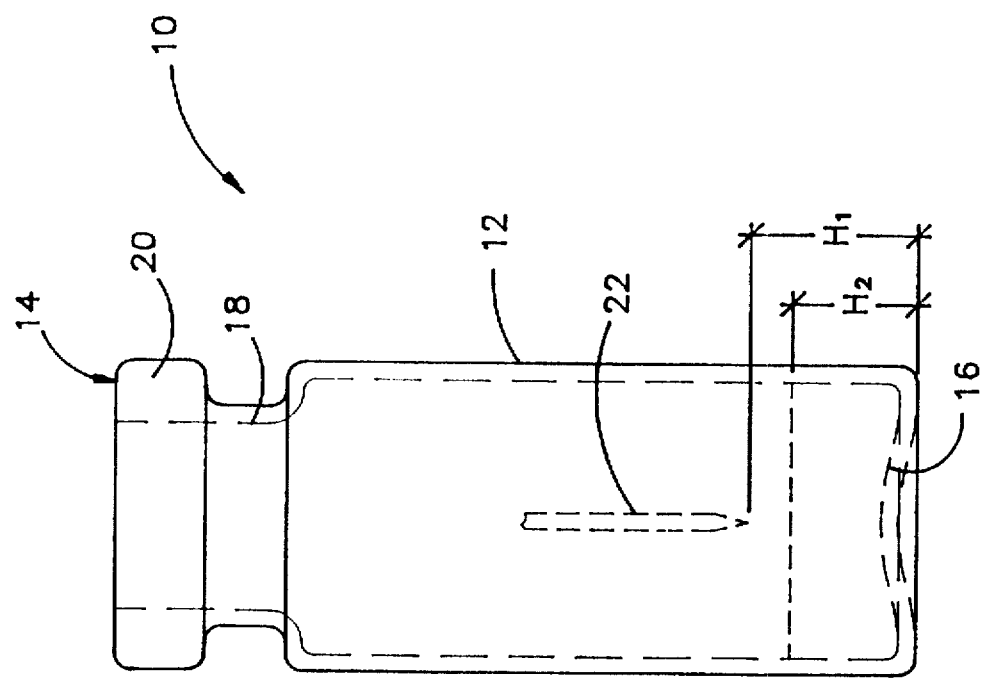
FIG. 1 is an elevation view of a conventional sampling vial.
Figure 2:
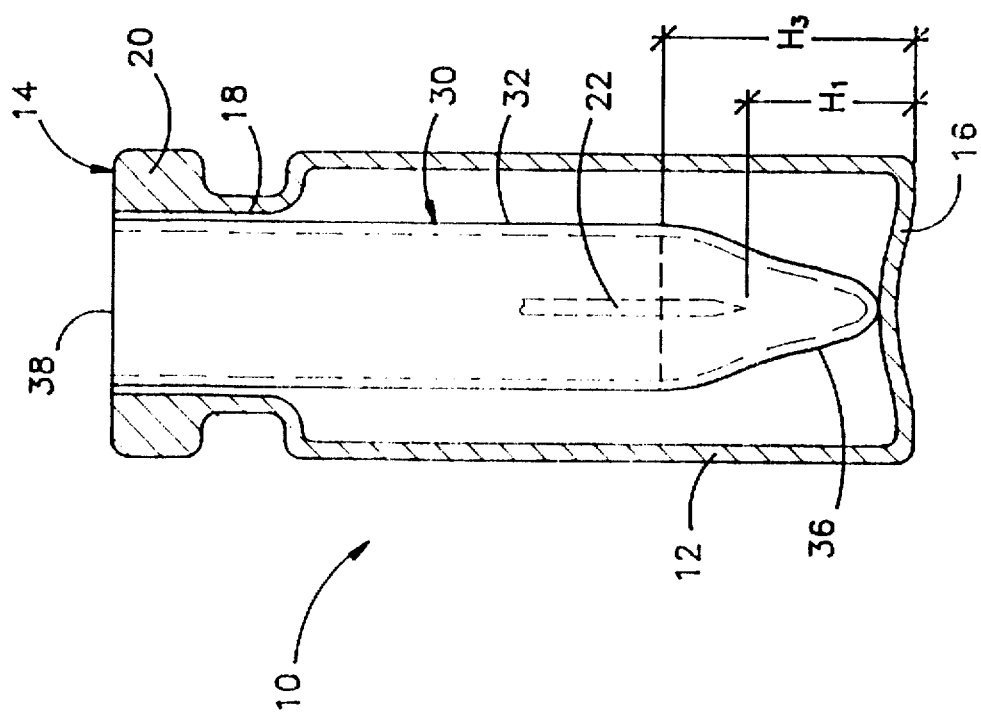
FIG. 2 is a section view of a conventional sampling vial with a vial insert disposed therein.
Figure 3:
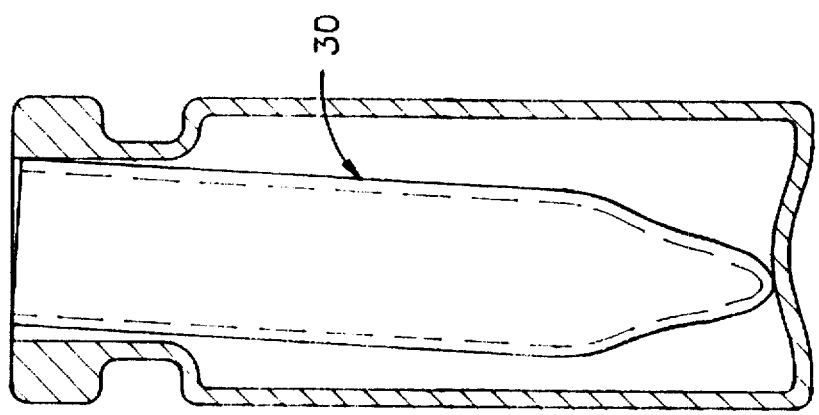
FIG. 3 is a section view of a conventional sampling vial with the vial insert shown in a tilted position.

FIGS. 1–3 of the drawings show a conventional prior art vial and vial insert used in autosampling applications. The prior art vial 10 includes a generally cylindrical body 12 and a standard crimp top indicated generally at 14. The crimp top 14 includes a relatively narrow neck 18 and an open collar 20. The neck 18 and collar 20 are designed so that a standard crimp cap (not shown) can be crimped onto the collar 20.

The vial 10 described above comes in a variety of sizes. For example, a standard 12 mm by 32 mm vial includes a main body 12 having an outside diameter of approximately 12 mm and an overall length of approximately 32 mm. Many autosamplers are designed to work with a standard 12 mm by 32 mm vial which has a volume of approximately 1.5 μl. The standard 12 mm by 32 mm vial works well with sample volumes above 250 μl. However, for sample volumes below 250 μl, there may be problems extracting the sample from the vial. As shown in FIG. 1, the autosampler needle 22 does not reach the bottom of the vial 10. The tip of the needle 22 is disposed at a height $H_1$ above of the bottom 16 of the vial. As a result, there is a dead volume between the bottom of the vial 16 and the tip of the needle 22. For small sample volumes, the liquid vial 10 rises to a height $H_2$ which is lower than the height $H_1$ of the needle 22. In this case, it is not possible to extract the sample using the standard 12 mm by 32 mm vial.

Referring now to FIG. 2, a conventional vial 10 is shown with a limited volume insert 30. The limited volume insert 30 is designed to allow microsampling of very small volumes. The vial insert 30 includes a generally cylindrical body 32 having a tapered portion 34 which terminates a closed tip 36. In the embodiment shown, the vial insert 30 has a straight top 38 although crimp top vial inserts are also known. The outside diameter of the vial insert 30 is slightly smaller than the opening 22 in the vial 10. The length of the vial insert 30 is matched with the vial 10 such that the top 38 of the insert is at or below the top of the vial 10.

The vial insert 30 is used primarily for microsampling. As shown in FIG. 2, the smaller interior diameter of the vial insert 30 results in a larger vertical displacement of the sample. For example, a sample which rises to a height $H_2$ in a conventional vial 10 (see FIG. 1) will rise to a height $H_3$ when a vial insert 30 is used thereby allowing the sample to be extracted. Further, the tapered configuration of the vial insert results in a greatly reduced dead volume.

One problem frequently encountered when using vial inserts 30 is that the vial insert 30 does not remain vertically oriented in the vial 10. The bottom 16 of the vial 10 typically is concave. This concave surface pushes the tip 36 of the vial insert 30 to one side, as seen in FIG. 3, causing the vial insert 30 to assume a tilted position. The present invention is designed to avoid this problem by providing a vial 40 particularly designed to hold the vial insert 30 in a vertically aligned position.

Figure 5:
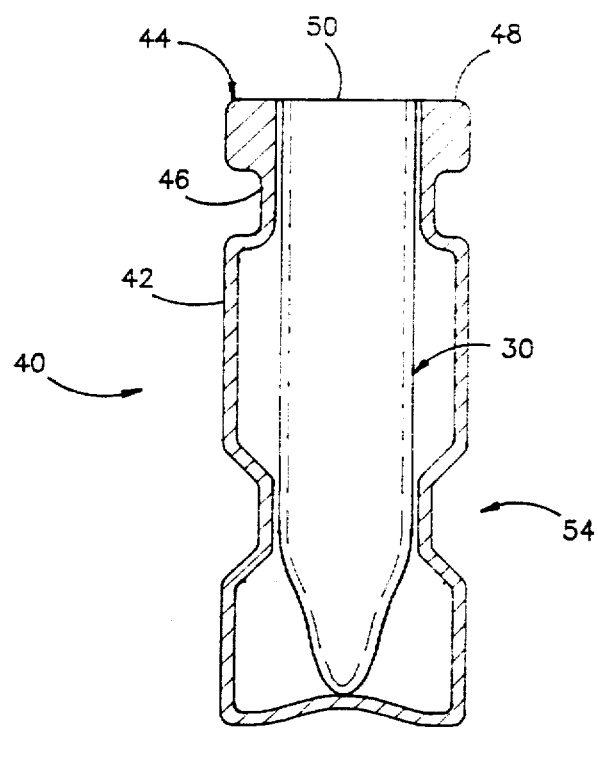
FIG. 5 is a section view thereof with a vial insert disposed therein.
Figure 4:
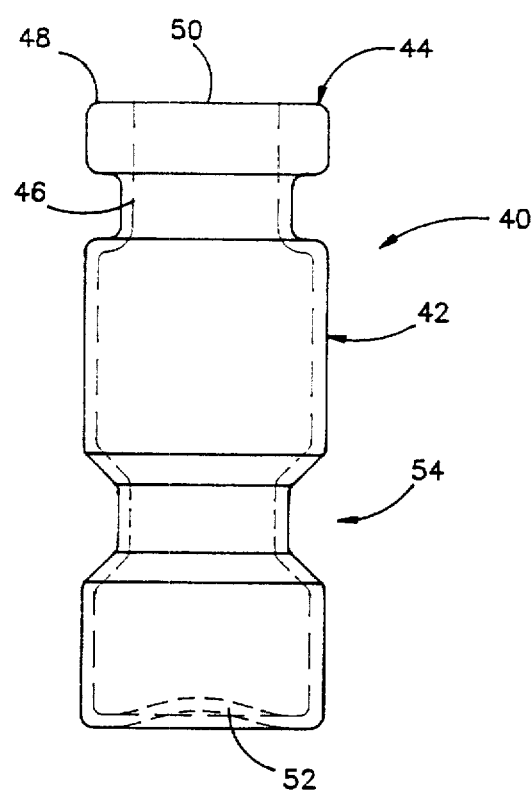
FIG. 4 is an elevation view of the sampling vial of the present invention.

Referring now to FIGS. 4 and 5, the improved vial 40 of the present invention is shown. The vial 40 of the present invention is made of soda lime glass or more preferably of a borosilicate glass. The vial 40 includes a generally cylindrical body indicated generally at 42 and a crimp top indicated generally at 44. The crimp top 44 comprises a reduced diameter neck 46 and an open collar 48 having an opening 50. Alternatively, other top finishes may be used such as a screw top (FIG. 6).

To the extent thus far described, the vial 40 is identical to the prior art vial shown in FIGS. 1 and 2. The vial 40 of the present invention differs from the prior art vial 10 in the provision of a reduced diameter section 54 in the main body section 42 of the vial 40. The reduced diameter section 54 is disposed approximately midway between the bottom 52 of the vial 40 and the neck 46. In the embodiment shown in FIGS. 4 and 5, the inside diameter of the reduced diameter section 54 is equal to the inside diameter of the neck 18. Preferably, the reduced diameter section 54 tapers inwardly from the outer surface of the vial 40.

Referring now to FIG. 5, the vial 40 of the present invention is shown with a limited volume insert 30. As shown in FIG. 4, the reduced diameter section 54 and the neck 18 of the vial 40 act as guides to axially align the vial insert 30 within the vial 40. Thus, the vial insert 30 will be held vertically without tilting. By precisely aligning the vial insert 30 along the vertical axis of the vial 40, there is a substantially reduced likelihood of damage to either the needle 22 or the vial insert 30.

Figure 6:
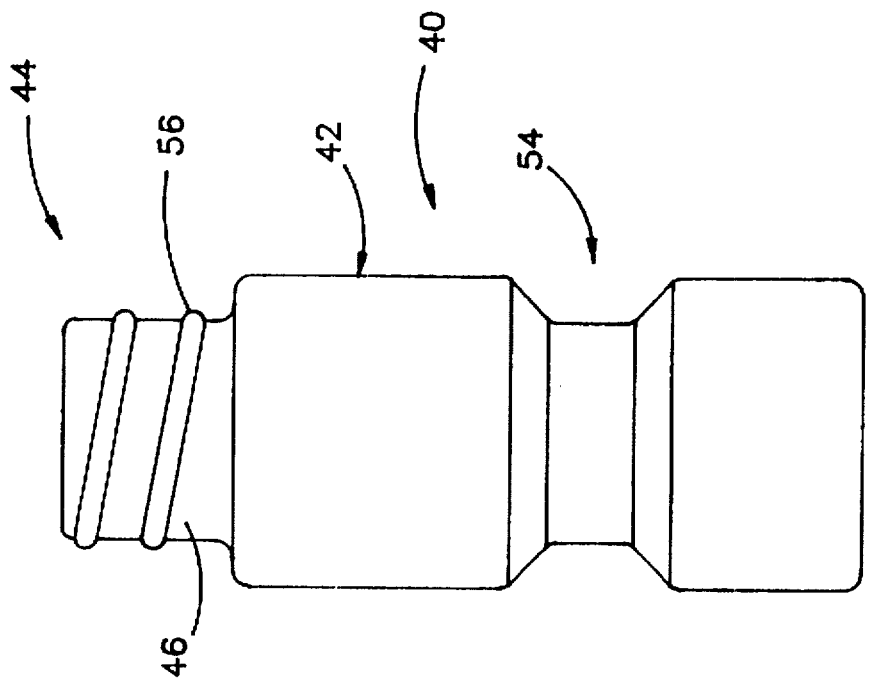
FIG. 6 is an elevation view of an alternate embodiment of the sampling vial of the present invention.

Referring now to FIG. 6, an alternate embodiment of the vial 40 is shown. The vial 40 shown in FIG. 6 includes a main body 42 having a reduced diameter section 54 and a reduced diameter neck 46. The embodiment shown in FIG. 6 includes external threads 56 on the neck 46 to receive a standard screw cap.

The vial 40 of the present invention can be used in the same manner as the conventional vial 10. The dimensions of the vial may be selected to fit into the sample tray of any commercially available autosampler. The vial 40 of the present invention may be used either with or without the vial insert 30. The reduced diameter section 54 will slightly reduce the volume of the vial 40 of the present invention as compared to a conventional vial of similar overall dimensions. Otherwise, the vial 40 of the present invention can be used in any application where a conventional vial of similar dimension can be used.

What is claimed is:

1. A chromatography sampling vial assembly comprising:
   a) an insert vial having a generally cylindrical main body and a closed bottom so as to form a receptacle for receiving a sample;
   b) a distinct glass chromatography carrier vial for receiving and holding said insert vial, said carrier vial including:
      i) a generally cylindrical main body including an upper section having a predetermined inner diameter and a lower section disposed along a longitudinal axis;
      ii) a head portion at an upper end of said main body, said head portion including a vial opening of a predetermined determined diameter axially aligned with said longitudinal axis;
      iii) a closed bottom positioned at said lower section having an inner diameter substantially the same as said predetermined inner diameter of said upper section so as to form a receptacle for receiving a sample; and
      iv) a reduced diameter mid-section between said upper section and said lower section of said main body; said mid-section having both a reduced inner diameter and a reduced outer diameter with respect to said main body of said carrier vial;
   c) wherein said reduced diameter mid-section is axially aligned with said vial opening for axially aligning said insert vial in said carrier vial when the insert vial is inserted into the carrier vial.

2. The sampling vial assembly of claim 1 wherein said insert vial is receivable in said carrier vial so as to pass through said reduced diameter mid-section and wherein said reduced diameter mid-section vertically aligns said insert vial along said longitudinal axis of said carrier vial.

3. The sampling vial assembly of claim 1 wherein said reduced diameter mid-section has the same inside diameter as the vial opening.

4. The sampling vial assembly of claim 1 wherein said head portion comprises a crimp top for receiving a crimp cap.

5. The sampling vial assembly of claim 1 wherein said head portion comprises a screw top for receiving a screw cap.

6. The sampling vial assembly of claim 1 wherein said head portion includes a reduced diameter neck joined to said main body at an upper end thereof.

7. The sampling vial assembly of claim 6 wherein said head portion includes a collar surrounding said neck portion.

8. The sampling vial assembly of claim 6 wherein said neck portion is externally threaded.

9. The sampling vial assembly of claim 1 wherein said insert vial includes a tapered end on a lower portion thereof.

10. A chromatography sampling vial assembly comprising:
    a) an insert vial having a generally cylindrical main body and a closed tapered bottom so as to form a receptacle for receiving a sample;
    b) a distinct glass chromatography carrier vial for receiving and holding said insert vial, said carrier vial including:
       i) a generally cylindrical main body including an upper section having a predetermined inner diameter and a lower section disposed along a longitudinal axis;
       ii) a head portion at an upper end of said main body including a vial opening of a predetermined diameter axially aligned with said longitudinal axis; said head portion comprising a crimp top for receiving a crimp cap
       iii) a closed bottom positioned at said lower section having an inner diameter substantially the same as said predetermined inner diameter of said upper section so as to form a receptacle for receiving a sample; and iv) a reduced diameter mid-section between said upper section and said lower section of said main body; said mid-section having both a reduced inner diameter and a reduced outer diameter with respect to said main body of said carrier vial;

c) wherein said reduced diameter mid-section is axially aligned with said vial opening and wherein said insert vial is receivable in said carrier vial so as to pass through said reduced diameter mid-section and wherein said reduced diameter mid-section vertically aligns said insert vial along said longitudinal axis of said carrier vial.

11. A chromatography sampling vial assembly comprising:

a) an insert vial having a generally cylindrical main body and a closed tapered bottom so as to form a receptacle for receiving a sample;

b) a distinct glass chromatography carrier vial for receiving and holding said insert vial, said carrier vial including:
  i) a generally cylindrical main body including an upper section having a predetermined inner diameter and a lower section disposed along a longitudinal axis;
  ii) a head portion at an upper end of said main body including a vial opening of a predetermined diameter axially aligned with said longitudinal axis; said head portion comprising a screw top for receiving a screw cap;
  iii) a closed bottom positioned at said lower section having an inner diameter substantially the same as said predetermined inner diameter of said upper section so as to form a receptacle for receiving a sample; and
  iv) a reduced diameter mid-section between said upper and lower sections of said main body; said reduced diameter mid-section having both a reduced inner diameter of the same size as said vial opening and a reduced outer diameter which is smaller than the outer diameter of said main body;

c) wherein said reduced diameter mid-section is axially aligned with said vial opening and wherein said insert vial is receivable in said carrier vial so as to pass through said reduced diameter mid-section and wherein said reduced diameter mid-section vertically aligns said insert vial along said longitudinal axis of said carrier vial.

\* \* \* \* \*